United States Patent [19]

Gottstein et al.

[11] 4,182,863
[45] Jan. 8, 1980

[54] 7-AMINO-3-(1-CARBOXYMETHYLTET-RAZOL-5-YLTHIOMETHYL)-3-CEPHEM-4-CARBOXYLIC ACID

[75] Inventors: William J. Gottstein, Fayetteville; Murray A. Kaplan, Syracuse; Alphonse P. Granatek, Baldwinsville, all of N.Y.

[73] Assignee: Bristol-Myers Company, New York, N.Y.

[21] Appl. No.: 712,111

[22] Filed: Aug. 5, 1976

Related U.S. Application Data

[60] Division of Ser. No. 590,971, Jun. 27, 1975, abandoned, which is a continuation-in-part of Ser. No. 502,991, Sep. 3, 1974, abandoned.

[51] Int. Cl.² ........................................... C07D 501/18
[52] U.S. Cl. ........................................ 544/26; 544/27; 424/246
[58] Field of Search ........................ 260/243 C; 544/26

[56] References Cited

U.S. PATENT DOCUMENTS

| 3,819,623 | 6/1974 | Takano et al. ................ 260/243 C |
| 3,989,694 | 11/1976 | Berges ............................. 260/243 C |

Primary Examiner—Nicholas S. Rizzo
Attorney, Agent, or Firm—Herbert W. Taylor, Jr.

[57] ABSTRACT

Certain 7-acylamido-3-(1-carboxymethyltetrazol-5-ylthiomethyl)-3-cephem-4-carboxylic acids and their salts and easily hydrolyzed esters of the 4-carboxyl group were synthesized and found to be potent antibacterial agents which exhibited good aqueous solubility. In a preferred embodiment the 7-substituent was 2'-aminomethylphenylacetamido.

11 Claims, No Drawings

7-AMINO-3-(1-CARBOXYMETHYLTETRAZOL-5-YLTHIOMETHYL)-3-CEPHEM-4-CARBOXYLIC ACID

CROSS-REFERENCE TO RELATED APPLICATIONS

This application is a division of our prior, copending application Ser. No. 590,971 filed June 27, 1975, now abandoned, which in turn was a continuation-in-part of prior, copending application Ser. No. 502,991 filed Sept. 3, 1974 and now abandoned.

BACKGROUND OF THE INVENTION

1. Field of the Invention

The cephalosporins of the present invention in general possess the usual attributes of such compounds and are particularly useful in the treatment of bacterial infections.

2. Description of the Prior Art

The cephalosporins are a well-known group of semisynthetic antibacterial agents made originally, for example, by acylation of the 7-amino group of the nucleus 7-aminocephalosporanic acid (7-ACA) and later by similar acylation of nuclei derived therefrom, as by modification of its substituent at the 3-position. Various reviews have appeared in the scientific literature (e.g. Cephalosporins and Penicillins—Chemistry and Biology, edited by Edwin H. Flynn, Academic Press, New York, 1972, and particularly pages 554–569) and in the patent literature, e.g. as in U.S. Pat. Nos. 3,687,948; 3,741,965; 3,743,644; 3,759,904; 3,759,905; 3,766,175; 3,766,906; 3,769,281; 3,796,801; 3,799,923; 3,812,116; 3,813,388; 3,814,754 and 3,814,755 (all U.S. Class 260–243C).

Issued patents on 3-thiolated cephalosporins in which the 7-substituent is (a) α-Amino-α-phenylacetamido include U.S. Pat. Nos. 3,641,021, 3,734,907, 3,687,948, 3,741,965, 3,757,015, 3,743,644, Japan No. 71/24400 (Farmdoc 46374S), Belgium No. 776,222 (Farmdoc 38983T; U.K. No. 1,328,340 which includes various substituents on the benzene ring), Belgium No. 772,592 (Farmdoc 19696T; U.S. Pat. Nos. 3,687,948, 3,734,907 and 3,757,012), West Germany 2,202,274 (Farmdoc 50428T) corresponding to U.S. Pat. No. 3,759,904, Netherlands 7205644 (Farmdoc 76309T; U.S. Pat. No. 3,757,014); and (b) o-, m- or p-aminoethoxyphenylacetamido as Netherlands 72/13968 (Farmdoc 24740U) corresponding to U.S. Pat. No. 3,759,905 and (c) o-aminomethylphenylacetamido as Netherlands 72/06326 (Farmdoc 76374T) (which also reviews the older patent literature concerning substituted 7-phenylacetamidocephalosporanic acids) corresponding to U.S. Pat. Nos. 3,766,176 and 3,766,175; and (d) N-(phenylacetimidoyl)aminoacetamido as U.S. Pat. No. 3,692,779; and (e) α-amino-α-(1,4-cyclohexadienyl)acetamido as in Belgium 766,222 (Farmdoc 38983T; U.K. Pat. No. 1,328,340).

Additional similar disclosures are found in U.S. Pat. No. 3,692,779 (Belgium 771,189; Farmdoc 12819I), Japan No. 72/05550 (Farmdoc 12921T), Japan No. 72/05551 (Farmdoc 12922T), U.S. Pat. No. 3,719,673 (Belgium 759,570; Farmdoc 39819S), Belgium No. 793,311 (Farmdoc 39702U) and Belgium No. 793,191 (Farmdoc 39684U).

Issued disclosures of 3-thiolated cephalosporins in which the 7-substituent is 7-mandelamido (7-α-hydroxyphenylacetamido) are found, for example, in U.S. Pat. No. 3,641,021, France No. 73.10112, U.S. Pat. No. 3,796,801, Great Britain No. 1,328,340 (Farmdoc 38983T), U.S. Pat. No. 3,701,775, Japan No. 4844293 (Farmdoc 55334U) and in Hoover et al., J. Med. Chem. 17(1), 34–41 (1974) and Wick et al., Antimicrobial Ag. Chemo., 1(3), 221–234 (1972).

U.S. Pat. No. 3,819,623 (and, for example, also U.K. No. 1,295,841 and West Germany No. 1,953,861) discloses specifically and with working details the preparation of 2-mercapto-1,3,4-thiadiazole-5-acetic acid and its conversion to 7-(1H-tetrazol-1-yl-acetamido)-3-(5-carboxymethyl-1,3,4-thiadiazol-2-ylthiomethyl)-3-cephem-4-carboxylic acid which is also disclosed in West Germany Offenlegungsschrift No. 2,262,262.

SUMMARY OF THE INVENTION

The present invention provides the compounds having the structure:

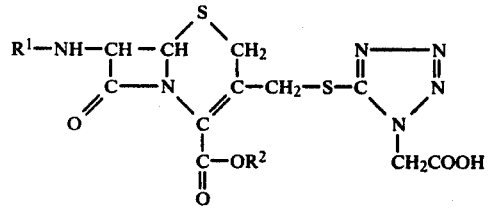

(often written herein as

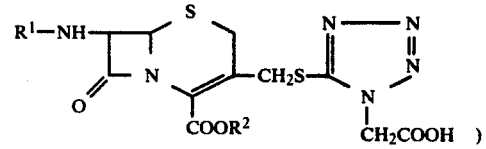

)

wherein $R^1$ is acyl or hydrogen and $R^2$ is hydrogen or the group having the formula

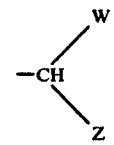

wherein, when W represents hydrogen, Z represents (lower)alkanoyl, benzoyl, naphthoyl, furoyl, thenoyl, nitrobenzoyl, methylbenzoyl, halobenzoyl, phenylbenzoyl, N-phthalimido, N-succinimido, N-saccharino, N-(lower)alkylcarbamoyl, (lower)alkoxy, (lower)alkylthio, phenoxy, carbalkoxy, carbobenzoxy, carbamoyl, benzyloxy, chlorobenzyloxy, carbophenoxy, carbo-tert.-butoxy or (lower)alkylsulfonyl, and when W represents carbalkoxy, Z represents carbalkoxy and, when W represents phenyl, Z represents benzoyl or cyano or wherein W and Z taken together represent 2-oxocycloalkyl containing 4 to 8 carbon atoms inclusive. In the preferred embodiments of this invention $R^2$ is hydrogen, pivaloyloxymethyl, acetoxymethyl, methoxymethyl, acetonyl, phenacryl, p-nitrobenzyl, β,β,β-trichloroethyl, 3-phthalidyl or 5-indanyl.

As set forth below in more detail the present invention also provides salts of these acids. The stereochemistry of the bicyclic nucleus is that found in Cephalosporin C.

Acyl (R¹) includes, but is not limited to, α-hydroxyphenylacetyl and α-aminophenylacetyl and ortho-aminomethylphenylacetamido.

Such salts include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)alkylpiperidine, e.g. N-ethylpiperidine, and other amines which have been used to form salts with benzylpenicillin.

The present invention also provides the process for the production of the antibacterial agents having the structure

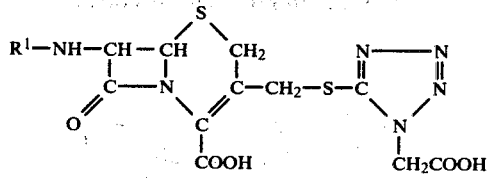

wherein R¹ is acyl which comprises reacting a compound of the formula

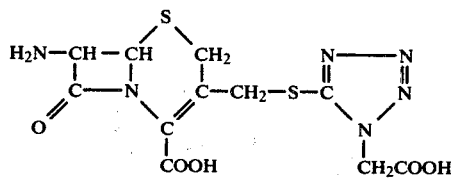

or a salt or easily hydrolyzed ester or Schiff base as with benzaldehyde or salicylaldehyde thereof (including, but not limited to, those of U.S. Pat. No. 3,284,451 and U.K. Pat. No. 1,229,453 and any of the silyl esters described in U.S. Pat. No. 3,249,622 for use with 7-aminopenicillanic acid and used in Great Britain No. 1,073,530 and particularly the pivaloyloxymethyl, acetoxymethyl, methoxymethyl, acetonyl, phenacyl, p-nitrobenzyl, β,β,β-trichloroethyl, 3-phthalidyl and 5-indanyl esters) thereof with an organic monocarboxylic acid chloride or a functional equivalent thereof as an acylating agent.

Such functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. A particularly useful anhydride is an N-carboxy-anhydride (also called a Leuch's anhydride; see U.S. Pat. Nos. 3,080,356 and 3,206,455) including but not limited to D-mandelic acid carboxyanhydride (U.S. Pat. No. 3,167,549) or the corresponding substituted D-mandelic acid carboxyanhydride. In addition, an acid azide or an active ester or thioester (e.g. with p-nitrophenyl, 2,4-dinitrophenol, thiophenol, thioacetic acid) may be used or the free acid itself may be coupled with compound II after first reacting said free acid with N,N'-dimethylchloroformiminium chloride [cf. Great Britain 1,008,170 and Novak and Weichet, *Experientia XXI*, 6, 360 (1965)] or by the use of enzymes or of an N,N'-carbonyldiimidazole or an N,N'-carbonylditriazole [cf. South African patent specification 63/2684] or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, *J. Amer. Chem. Soc.*, 77, 1967 (1955)], or or alkylylamine reagent [cf. R. Buijle and H. G. Viehe, *Angew. Chem. International Edition* 3, 582, (1964)] or of an isoxasolium salt reagent [cf. R. B. Woodward, R. A. Olofson and H. Mayer, *J. Amer. Chem. Soc.*, 83, 1010 (1961)], or of a ketenimine reagent [cf. C. L. Stevens and M. F. Munk, *J. Amer. Chem. Soc.*, 80, 4065 (1958)] or of hexachlorocyclotriphosphatriazine or hexabromocyclotriphosphatriazine (U.S. 3,651,050) or of diphenylphosphoryl acide [DPPA; *J. Amer. Chem. Soc.*, 94, 6203–6205 (1972)] or of diethylphosphoryl cyanide [DEPC; *Tetrahedron Letters* No. 18, pp. 1595–1598 (1973)] or of diphenyl phosphite [*Tetrahedron Letters* No. 49, pp. 5047–5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The by-product, imidazole, precipitates and may be separated and the imidazolide isolated, but this is not essential. The methods for carrying out these reactions to produce a cephalosporin and the methods used to isolate and cephalosporin so produced are well known in the art.

Mention was made above of the use of enzymes to couple the free acid with compound II. Included in the scope of such processes are the use of an ester, e.g. the methyl ester, of that free acid with enzymes provided by various micro-organisms, e.g. those described by T. Takahashi et al., *J. Amer. Chem. Soc.*, 94(11), 4035–4037 (1972) and by T. Nara et al., J. Antibiotics (Japan) 24(5), 321–323 (1971) and in U.S. Pat. No. 3,682,777.

For the coupling of the organic carboxylic acid, including but not limited to a substituted or unsubstituted D-mandelic acid (with or without a protecting group on the α-hydroxyl), as described above with compound II (or a salt or preferably an easily hydrolyzed ester of Schiff base, as with benzaldehyde, thereof) it is also convenient and efficient to utilize as the coupling agent phosphonitrilic chloride trimer (J. Org. Chem., 33(7), 2979–81, 1968) or N-ethoxy-1,2-dihydroquinoline (EEDQ) as described in J. Amer Chem. Soc., 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a 7-acylaminocephalosporanic acid (prepared by substituting 7-aminocephalosporanic acid for the 3-thiolated-7-aminocephalosporanic acids in the acylation procedures described herein and elsewhere reported) with a thiol having the formula

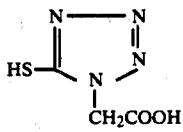

and then removing the protecting group if any is present, as on an α-hydroxy or α-amino or the like or on the carboxyl group or both. The displacement of such a 3-acetoxy group with such a thiol may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. To provide some specific examples for purposes of illustration but not of limitation, substituted or unsubstituted D-mandelamido-cephalosporanic acids are prepared by the procedures described generally or specifically in J. Med. Chem. 17(1), 34–41 (1974) and the references cited therein. As noted above, the preparation of many other 7-acylamidocephalosporanic acids is described in the patent and scientific literature, e.g. in U.S. Class 260-243C.

When the organic carboxylic acid contains a functional group such as amino or hydroxyl it is often desirable to first block (or protect) the amino or hydroxy group, then carry out the coupling reaction and finally subject the resulting compound to chemical removal of the protecting group, that is, subjecting the resulting compound to elimination reaction of the protecting group.

The term "(lower)alkyl" as used herein means both straight and branched chain aliphatic hydrocarbon radicals having from one to ten carbon atoms such as methyl, ethyl, propyl, isopropol, butyl, isobutyl, t-butyl, amyl, hexyl, 2-ethylhexyl, heptyl, decyl, etc. Similarly, where the term "(lower)" is used as part of the description of another group, e.g. "(lower)alkoxy", it refers to the alkyl portion of such group which is therefore as described above in connection with "(lower)alkyl".

The present invention thus also provides the process for the production of the antibacterial agents having the structure

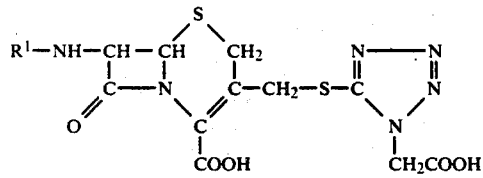

wherein R¹ is acyl which comprises reacting a compound having the formula

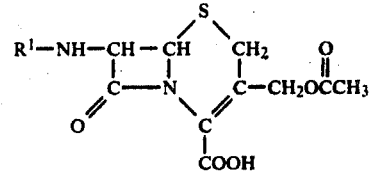

wherein R¹ is acyl (including cephalosporin C itself) with a compound having the formula

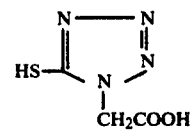

In the case of the compounds having a substituted amino group in the 7-side chain it is often desirable to prepare first the compound containing an unsubstituted (free or primary) amino group and then react that product with the appropriate reagent to produce final products of the type illustrated above in the definitions of acyl groups under viii, xvii and xviii as appropriate.

The present invention also provides the process for the production of the novel and valuable intermediate having the structure

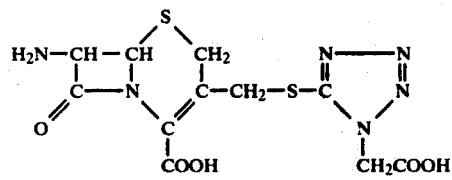

which comprises removing the 7-side chain from a reagent having the structure

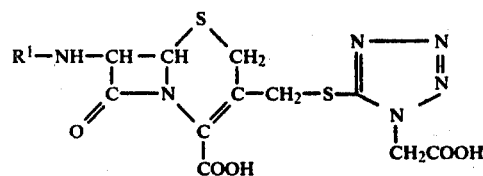

wherein the acyl group (R¹) is one of those defined above by converting said reagent, preferably in silylated form, to an imino-chloride (as with PCl₅) and thence to an imino-ether (as with methanol) and thence to the desired product by hydrolysis (as with water). Details for the conduct of such reactions are known to the art and taught, for example, in U.S. Pat. Nos. 3,575,970; 3,573,295 and 3,573,296.

The present invention also provides the process for the production of the novel and valuable intermediate having the structure

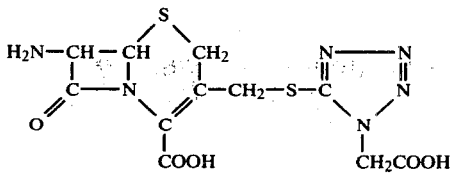

which comprises reacting 7-aminocephalosporanic acid or a salt or easily hydrolyzed ester or Schiff base thereof with a compound having the formula

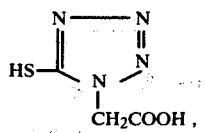

also called HSR² herein,

Such salts include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)alkylpiperidine, e.g. N-ethylpiperidine, and other amines which have been used to form salts with benzylpenicillin; and the nontoxic acid addition salts thereof (i.e., the amine salts) including the mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate and the like.

Also included in this invention are the compounds (used as either intermediates or metabolic precursors) in which the amino group is "blocked" by substituents such as 2-iodoethoxycarbonyl (U.K. Pat. No. 1,349,673), t-butoxycarbonyl, carbobenzyloxy, formyl, o-nitrophenylsulfenyl, β,β,β-trichloroethoxycarbonyl, 4-oxo-2-pentenyl-2, 1-carbomethoxy-1-propenyl-2- and the like. Particularly included in such blocking groups are the ketones (especially acetone) and aldehydes (especially formaldehyde and acetaldehyde) disclosed, for example, in U.S. Pat. Nos. 3,198,804 and 3,347,851 and the β-ketoesters and β-diketones disclosed, for example, in U.S. Pat. No. 3,325,479 and the β-ketoamides disclosed in Japan 71/24714 (Farmdoc 47,321S).

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group.

As indicated above, these five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767–773 (1971). In another good method the triethylamine salt of 7-aminocephalosporanic acid is reacted directly with the active halogen compound, as in United Kingdom No. 1,229,453.

These esters of 7-aminocephalosporanic acid are then reacted with the nucleophile HSR² in the same manner as is illustrated herein for 7-aminocephalosporanic acid itself. The 3-thiolated ester of 7-aminocephalosporanic acid is then coupled with the organic carboxylic acid, e.g. D-(−)-2-phenylglycine, as before. Before or after removal of any blocking group, e.g. on an amino or hydroxy group in the 7-sidechain, the ester of the cephalosporin so obtained is, if not used per se, converted to its free acid, including its zwitterion (and, if desired, any salt) by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006–2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

The present invention also provides the process for the production of the novel and valuable intermediate having the structure

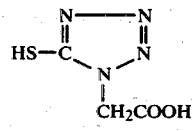

which comprises forming in an anhydrous solvent the lithio derivative of a thiol of the formula

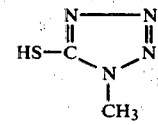

and reacting said lithio derivative with carbon dioxide to form a product which is then hydrolyzed to give the compound of the formula

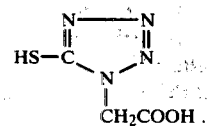

In the treatment of bacterial infections in man, the compounds of this invention are administered parenterally in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excepients. The dosage units are in the form of liquid preparations such as solutions or suspensions.

STARTING MATERIALS

A. 1-Carboxymethyl-5-mercaptotetrazole

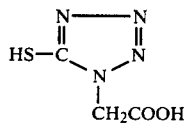

(a) Recrystallization of 1-methyl-5-mercaptotetrazole
Procedure:

1. One hundred and ten grams of 1-methyl-5-mercaptotetrazole is slurried in 350 ml. of boiling chloroform. A near solution is obtained.
2. The hot solution (50°–60°) is rapidly filtered by vacuum through a heated Buchner funnel (11 cm. SS. No. 604 paper containing ¼ to ⅓ inch of packed filter aid ("Supercel"). The filter pad is washed with 50 ml. of 50°–60° C. chloroform which is added to the filtrate.
3. The filtrate is cooled to approximately 0°–6° C. and kept at 0°–6° C. for 2 hours. The crystals which have formed are collected by filtration at 0°–6° C. and washed with 60 ml. of 0°–6° C. chloroform which is added to the filtrate. The crystals (cut A) are air dried at 37°–45° C. for 18 hours.
4. The filtrate is concentrated on the rotary vacuum evaporator (60° C. bath) to approximately one-half volume. This slurry is cooled to 0°–6° C. and kept at 0°–6° C. for 2 hours. The crystals are collected by filtration at 0°–6° C., washed with 40 ml. of 0°–6° C. chloroform which is added to the filtrate. The crystals (cut B) are air dried at 37°–45° C. for 18 hours. Crystal cuts A and B are composited to give an approximate 65% weight yield.
5. The filtrate of cut B, Step 4 may be reworked twice as described in Step 4 to obtain an additional 15% recovery.

(b) Preparation of the Di-sodium Salt of 1-carboxymethyl-5-mercaptotetrazole
Procedure:

1. Five hundred ml. of substantially dry and pure tetrahydrofuran in a 2-liter 3 neck flask with stirrer is cooled in a salt-acetone-ice bath to approximately −10° C. Dry nitrogen gas is blown on the liquid surface.
2. Five hundred ml. of 15.06% (1.6 N) butyl lithium in hexane (Foote Mineral Co.) is added over a ten minute period under dry nitrogen and stirring to the tetrahydrofuran. The near solution is cooled to −5° to −10° C.
3. Forty six and four tenths gram (46.4 g.) of 1-methyl-5-mercaptotetrazole (recrystallized as above) is dissolved in 200 ml. of substantially pure and dry tetrahydrofuran. The solution is filtered if cloudy and then cooled to 5° to 10° C.
4. The cooled solution of step 3 is added over 10 minutes with stirring and under dry nitrogen to the butyl lithium solution. The temperature should be maintained at −5° C. to +10° C. maximum. Precipitates may form.
5. The mixture is stirred under dry nitrogen and 0° C. to +10° C. for one half hour.
6. Anhydrous carbon dioxide gas is bubbled through at a rapid rate and with rapid stirring for 15-30 minutes at approximately ambient temperature (0° to 10° C.) to no higher than +20° C.
7. The white precipitate which forms is suitably collected by filtration in an area of low humidity. The precipitate is washed with about 75 ml. of tetrahydrofuran.
8. The precipitate is dissolved in 250 ml. of water (pH 8.5–9.5). A second layer of tetrahydrofuran may be present. This may be removed in the vacuum rotary evaporator (50° C. bath).
9. The aqueous solution is adjusted to pH 1.6–2.0 with concentrated hydrochloric acid.
10. The acid aqueous solution is extracted twice with 250 ml. portions of ethyl acetate. Each 250 ml. ethyl acetate extract is back extracted with 100 ml. portions of water. The water extracts are discarded. The ethyl acetate extracts (free of any water layer) are filtered and composited.
11. The combined ethyl acetate extracts are concentrated to dryness on the vacuum rotary evaporator (60° C. bath).
12. The crystals in the flask are boiled with 300 ml. of chloroform for about 2 minutes. The hot slurry (50°–60° C.) is vacuum filtered through a heated Buchner funnel (11 cm-SS-604 paper). The crystals are washed with about 75 ml. of 50° C. chloroform. The crystals are air dried at room temperature for about 3 hours and then made about 100–200 mesh.
13. The 100–200 mesh crystals are treated with boiling chloroform exactly as described in step 12 (the hot chloroform removes most of the unreacted 1-methyl-5-mercaptotetrazole). Yield: approximately 45 to 50 grams of crystalline 1-carboxymethyl-5-mercaptotetrazole. These crystals may contain 0.02 to 0.05 moles of 1-methyl-5-mercaptotetrazole.
14. The crystals of step 13 are slurried with 250 ml. of ethyl ether at room temperature for 3–5 minutes. The mixture is filtered. The insolubles (0.5–5%) may be a contaminating symmetrical mercaptotetrazole ketone of the following tentative structure:

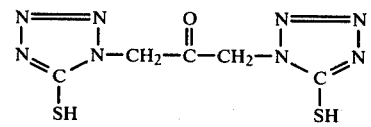

CAUTION: This compound EXPLODES at approximately 205°–210° C.

15. The ether filtrate of step 14 is evaporated to dryness on the vacuum rotary evaporator (50° C. bath). Approximately 42 to 48 grams of crystalline 1-carboxymethyl-5-mercaptotetrazole containing approximately 0.01–0.05 mole of 1-methyl-5-mercaptotetrazole is recovered.
16. The crystals are dissolved in 420 ml. of absolute ethanol (approximately 100 mg./ml.). The solution is warmed to 50°–60° C.
17. To the hot solution of step 16, 310 ml. of a 41% sodium 2-ethylhexanoate (SEH) solution in isopropanol is added with very rapid stirring over a 10 minute period. A crystalline precipitate forms. The mixture is slurried at 50°–60° C. for 20 minutes.
18. The mixture is filtered hot (50°–60° C.) through a heated Buchner funnel (11 cm-SS-No. 604 paper). The crystals are washed with 75 ml. of 50° C. ethanol.
19. The ethanol damp crystals of step 18 are slurried in 200–300 ml. of ethanol. The slurry is passed through a 200 mesh screen. The slurry is heated to 50°–60° C. for 5 minutes with rapid stirring (unreacted di-sodium 1- methyl-5-mercaptotetrazole is very soluble in hot ethanol).

20. The crystals are collected at 50°–60° C. on a 11 cm-SS No. 604 paper in a heated Buchner funnel. The crystals are washed with 75–100 ml. of ethanol and vacuum dried at 50°–60° C. for 24–48 hours. Yield: 40–48 grams of di-sodium 1-carboxymethyl-5-mercaptotetrazole (free of 1-methyl-5-mercaptotetrazole as observed by NMR).

B.
7-Amino-3-(1-carboxymethyltetrazol-5-ylthiomethyl)-3-cephem-4-carboxylic acid.

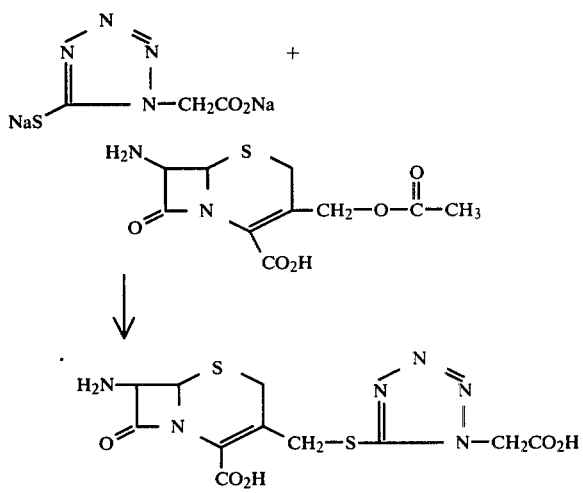

1. Into a 3 necked flask set up with an agitator, a temperature regulator, thermometer and a nitrogen inlet tube, place 18 grams (0.066 mole) of 7-aminocephalosporanic acid, (which has preferably has recrystallized by the toluenesulfonic acid procedure) and 300 ml. of 0.1 M pH 6.4 phosphate buffer (20.7 grams of sodium phosphate, monobasic .1H$_2$O+8.5 grams of sodium phosphate, dibasic, anhydrous, q.s. to 2 liters).

2. With agitation of the mixture described in step 1, add 1.5 grams of sodium bisulfite and 16 grams (0.078 moles) of 1-carboxymethyl-5-mercaptotetrazole disodium.

3. With agitation continuing, bubble nitrogen through the mixture for 10 minutes.

4. Maintaining agitation and nitrogen inflow, heat the slurry over a 20 minute period to 56° C. During this time interval, 6.5 grams of sodium bicarbonate is added in small increments.

5. With continued agitation and nitrogen inflow, maintain the temperature of the solution at 56° C. for 4 hours. The pH should remain at between 6.2–6.6.

6. Cool the reaction mixture in an ice bath to 5° C.

7. Add 50 ml. of a 1:1 phosphoric acid/water solution to the mixture or concentrated HCl to a pH of 2.0–3.0.

8. Collect the product by filtration. Wash the filter cake with 20 ml. of cold water followed by 200 ml. of cold methanol.

9. Air dry the solid to constant weight. (A typical run produced 14.5 grams of product.) This product may vary in color from yellow to dark brown.

10. Pass the product through a 200 mesh stainless steel screen.

11. Suspend 10 grams of the 200 mesh powder in 200 ml. of n-propanol with rapid stirring.

12. Add 2.0 ml. of concentrated hydrochloric acid and stir vigorously for 0.5 hours at room temperature.

13. Filter the slurry. Wash the brown solids with 20 ml. of n-propanol and add the wash to the filtrate (save the filter cake for possible recovery of additional product).

14. Add 1.5 grams of charcoal ("Darco G-60") to the n-propanol filtrate of step 13. Slurry for 0.5 hour. Remove the carbon by filtration. Wash the carbon with 20 ml. of n-propanol and add the wash to the filtrate.

15. With rapid stirring, add triethylamine to the n-propanol filtrate to an apparent pH of 3.0. Crystals form. Slurry for 10 minutes 16. Collect the white crystals by filtration and wash with 30 ml. of n-propanol, 50 ml. of methanol, and vacuum dry at 40° C. for 24 hours. Yields: 4 to 8 grams of 7-amino-3-(1-carboxymethyltetrazol-5-ylthiomethyl)-3-cephem-4-carboxylic acid.

17. An alternate procedure for the purification of 7-amino-3-(1-carboxylmethyltetrazol-5-ylthiomethyl)-3-cephem-4-carboxylic acid follows:

(a) Slurry 10 grams of the 200 mesh product (from step 10) in 75 ml. of 1 N hydrochloric acid for 10–15 minutes at room temperature. Filter to remove dark brown solids.

(b) Add 2.5 grams of charcoal ("Darco G-60") and slurry for 0.5 hour.

(c) Remove the carbon by filtration. Wash the carbon with 15 ml. of water and add the wash to the filtrate.

(d) With rapid stirring, add concentrated ammonium hydroxide to the filtrate to pH 2.5–3.0. Crystals form.

(e) Slurry the crystal mass for 25 minutes. Remove the crystals by filtration. Wash the crystals with 30 ml. of water, 50 ml. of methanol, and vacuum dry at room temperature. Yield: 4–7 grams of near white crystals.

The other reagents used to prepare the compounds of the present invention are synthesized either as described in the art (e.g. as in the patents and publications noted above) or by strictly analogous procedures.

Among the most active compounds of the present invention are those having the D configuration at the α-carbon atom in the 7-side chain, that is, those made from D-2-phenylglycine or D-mandelic acid or a monosubstituted D-2-phenylglycine or D-mandelic acid as illustrated herein. In addition, the configuration at the two optically active, asymmetric centers in the β-lactam nucleus is that found in cephalosporin C produced by fermentation and in the 7-aminocephalosporanic acid derived therefrom.

The following examples are given in illustration of, but not in limitation of, the present invention. All temperatures are in degrees Centigrade. 7-Aminocephalosporanic acid is abbreviated as 7-ACA; -ACA-represents the moiety having the structure

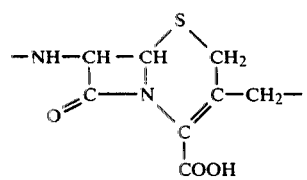

and thus 7-ACA can be represented as

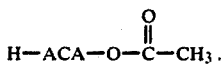

Methyl isobutyl ketone is represented as MIBK. "Skellysolve B" is a petroleum ether fraction of B.P. 60°-68° C. consisting essentially of n-hexane.

LA-1 resin is a mixture of secondary amines wherein each secondary amine has the formula

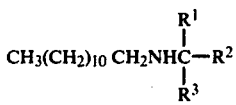

wherein each of $R^1$, $R^2$ and $R^3$ is a monovalent aliphatic hydrocarbon radical and wherein $R^1$, $R^2$ and $R^3$ contain in the aggregate from eleven to fourteen carbon atoms. This particular mixture of secondary amines, which is sometimes referred to in these examples as "Liquid Amine Mixture No. II," is a clear amber liquid having the following physical characteristics: viscosity at 25° C. of 70 cpd., specific gravity at 20° C. of 0.826; refractive index at 25° C. of 1.4554; distillation range at 10 mm., up to 170° C.—0.5%, 170°-220° C.—3%, 220°-230° C.—90% and above 230° C.—6.5%.

IR-120 is also called Amberlite IR-120 and is a strong cation exchange resin containing sulfonic acid radicals. Amberlite IR-120 is a commercially available cation exchange resin of the polystyrene sulfonic acid type; it is thus a nuclear sulfonated polystyrene resin cross-lined with divinyl benzene obtained by the procedure given by Kunin, Ion Exchange Resins, 2nd. Edition (1958), John Wiley and Sons, Inc. Therein see pages 84 and 87 for example.

DESCRIPTION OF THE PREFERRED EMBODIMENTS

EXAMPLE 1

7-(2-Aminomethylphenylacetamido)-3-(1-carboxymethyltetrazol-5-ylthiomethyl)-3-cephem-4-carboxylic acid

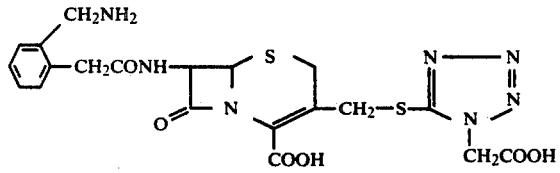

1. Into a 3 necked flask containing 100 ml. of deionized water and set up with an agitator and thermometer, add 7.6 grams (0.021 mole) of 7-amino-3-(1-carboxymethyltetrazol-5-ylthiomethyl)-3-cephem-4-carboxylic acid and 3.4 grams (0.034 mole) of N-methylmorpholine. Cool to 0° C. With agitation, the solution is maintained at 0° C. using an ice bath.

2. In a separate flask set up with an agitator, add 9.6 grams (0.03 mole) of sodium 2-(1-methoxycarbonyl-1-propen-2-ylaminomethyl)phenylacetate and 184 ml. of tetrahydrofuran. With agitation, the suspension is cooled to −30° C., using a dry ice acetone bath. Maintaining agitation and temperature at −30° C., add 20 drops of dimethylbenzylamine and 4.4 grams (0.03 mole) of isobutyl chloroformate. Stir the resulting mixture for 5 minutes.

3. Add all of the mixture from step 2 to the agitation solution in step 1 at one time. The resulting solution is maintained at 3° C. with agitation for 1 hour.

4. Evaporate the tetrahydrofuran from the reaction mixture at 30° C. using vacuum (15 mm).

5. Adjust the pH of the remaining aqueous solution to 4.0 using concentrated hydrochloric acid.

6. Add 2.5 grams of charcoal ("Darco G-60") to the solution and mix for 20 minutes. Remove the carbon by filtration.

7. The filtrate is layered with 120 ml. of ethyl acetate and with agitation the pH is lowered to 3.8 with concentrated hydrochloric acid. Some light tan colored solids may separate and are removed by filtration. (Save for reworking and recovery).

8. Using an ice bath, the filtrate is cooled to 5° C. and with agitation the pH is lowered to 2.5–2.8 with concentrated hydrochloric acid. Maintain the temperature at 5° C. and continue agitation for 1 hour.

9. Collect the product by filtration. Wash the filter cake with 5 ml. of cold deionized water followed by 5 ml. of cold methanol.

10. Air dry the solid 7-(2-aminomethylphenylacetamido)-3-(1-carboxymethyltetrazol-5-ylthiomethyl)-3-cephem-4-carboxylic acid to constant weight. (A typical run produced 4.1 grams of product).

11. The product as obtained from step 10 is passed through a 200 mesh stainless steel screen.

12. Ten grams of this 200 mesh product is slurried in 100 ml. of chloroform. Five ml. of triethylamine is added and the mixture is heated to 50° C. with rapid stirring. The mixture is slurried at 50° C. for 5 minutes.

13. The mixture is filtered hot (7-ACA, 7-amino-3-(1-carboxymethyltetrazol-5-ylthiomethyl)-3-cephem-4-carboxylic acid, pigments and other impurities are soluble in the hot chloroformtriethylamine solution). The filter cake is washed with 25 ml. of chloroform and air dried for 2 hours. Yield: 1–8 grams of 7-(2-aminomethylphenylacetamido)-3-(1-carboxymethyltetrazol-5-ylthiomethyl)-3-cephem-4-carboxylic acid.

14. The product as obtained for step 13 is passed through a 200 mesh screen.

15. Ten grams of this 200 mesh product is slurried in 75 ml. of 0.1 N hydrochloric acid for 10–15 minutes. The mixture is filtered and the filter cake is washed with 25 ml. of water, 50 ml. of methanol, and air dried at room temperature for 2–3 hours. Yield: Up to 10 g. is obtained.

16. Ten grams of 7-(2-aminomethylphenylacetamido)-3-(1-carboxymethyltetrazol-5-ylthiomethyl)-3-cephem-4-carboxylic acid as obtained from step 15 is slurried in 65 ml. of methanol.

(a) Two ml. of concentrated hydrochloric acid is added. A solution or near solution is obtained. Stir for 5 minutes.

(b) One hundred and 30 ml. of water is rapidly added with vigorous stirring to the solution of (a) above. An instantaneous precipitate (containing most of the color) is obtained. (A pH of 1.3 to 1.6 is required.)

(c) The mixture is slurried for 1 minute and rapidly filtered. (Save solids for rework and recovery.)

(d) The filtrate is seeded and moderately stirred. The onset of crystallization is about 15–30 minutes.

(e) The mixture is stirred at ambient room temperature or at 4° C. for 2 hours after the onset of crystallization.

(f) The crystals are removed by filtration, washed with 25 ml. of 65% water, 35% methanol mixture (v/v), 50 ml. of methanol, and vacuum dried at 50° C. for 24 hours. Yield: Up to 9 grams of purified, white 7-(2-aminomethylphenylacetamido)-3-(1-carboxymethyltetrazol-5-ylthiomethyl)-3-cephem-4-carboxylic acid is obtained.

17. The following are two alternate procedures for the crystallization of 7-(2-aminomethylphenylacetamido)-3-(1-carboxymethyltetrazol-5-ylthiomethyl)-3-cephem-4-carboxylic acid (A)

1. Ten grams of product as obtained from step 15 is slurried in 100 ml. of methanol.
2. Two ml. of concentrated hydrochloric acid is added and a solution or near solution is obtained.
3. One and five tenths gram of charcoal ("Darco G-60") is added and the mixture is slurried for 0.5 hour.
4. The carbon is removed by filtration and washed with 20 ml. of methanol. The methanol wash is added to the filtrate.
5. One hundred and twenty ml. of water is added to the filtrate. (A small amount of precipitate may come out. This is removed by filtration and saved for rework-recovery.)
6. The solution of step 5 is rapidly stirred and adjusted to pH 2.5–3.0 with 10% sodium hydroxide. Crystals form.
7. The mixture is slurried for 0.5 hour. The crystals are removed by filtration, washed with 20 ml. of 50% methanol-water (v/v), 30 ml. of methanol and vacuum dried at 50° C. for 24 hours. Yield: Up to 9 grams of purified 7-(2-aminomethylphenylacetamido)-3-(1-carboxymethyltetrazol-5-ylthiomethyl)-3-cephem-4-carboxylic acid is obtained.

(B)

1. Ten grams of product as obtained from step 15 is slurried in 75 ml. of water.
2. Ten percent sodium hydroxide is added to a maintained pH of 6.8–7.2. A solution or partial solution may be obtained.
3. One and five tenths grams of charcoal ("Darco G-60") is added and the mixture is slurried for 0.5 hour at a maintained pH of 6.8–7.2 (continued addition of 0.1 to 1 N sodium hydroxide).
4. The carbon is removed by filtration. The carbon is washed with 20 ml. of water which is added to the filtrate.
5. The pH 6.8–7.2 solution of step 4 may be crystallized at pH 2.5–3.0 as described in steps 6 and 7 of A, above or at pH 1.2–1.5 (by addition of hydrochloric acid) and as described in d, e, and f of step 16. In both instances, up to 9 grams of crystalline 7-(2-aminomethylphenylacetamido)-3-(1-carboxymethyltetrazol-5-ylthiomethyl)-3-cephem-4-carboxylic acid is obtained. This product is frequently obtained as a crystalline monohydrate.

EXAMPLE 2

Dipotassium 7-(D-α-hydroxyphenylacetamido)-3-(1-carboxymethyltetrazol-5-ylthiomethyl)-3-cephem-4-carboxylate

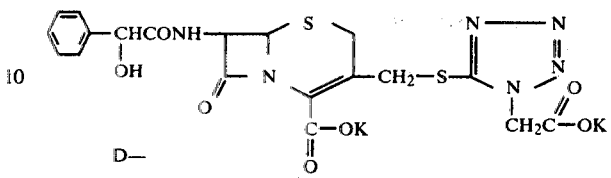

To a suspension of 500 mg. (0.0134 mole) of 7-amino-3-(1-carboxymethyltetrazol-5-ylthiomethyl)-3-cephem-4-carboxylic acid in 10 ml. of water at 0° was added with stirring 200 mg. of sodium bicarbonate. As soon as the solution was complete 340 mg. (0.172 mole) of D-(−)-2-formyloxy-2-phenylacetyl chloride was added all at once in 10 ml. of acetone. As soon as a precipitate formed, solid sodium bicarbonate was added and the solution was stirred at pH 8 for 1 hr. The acetone was evaporated at 15 mm at 30°, and the solution was layered with 20 ml. of ethyl acetate and acidified with 1:1 phosphoric acid. After extraction with ethyl acetate, the mixture was filtered and the organic layer was separated. The ethyl acetate was evaporated to a solid which was dissolved in 5 ml. of methanol and 5 drops of conc. hydrochloric acid. The solution was treated with carbon and heated for 3 min. on the steambath. The mixture was filtered and diluted with 15 ml. of water. The gummy solid was triturated with cold water and finally with anhydrous ether. The solid was dissolved in 5 ml. of acetone and was treated with 50 mg. of potassium 2-ethylhexanoate. Dipotassium 7-(D-α-hydroxyphenylacetamido)-3-(1-carboxymethyltetrazol-5-ylthiomethyl)-3-cephem-4-carboxylate, as a white solid, was collected and weighed 90 mg. m.p. 175° slow decomp.

Anal. Calcd. for $C_{19}H_{16}K_2N_6O_7S_2$: C, 39.19; H, 2.77; N, 14.42. Found: C, 39.87; H, 3.50; N, 12.58.

EXAMPLE 3

7-(D-α-Aminophenylacetamido)-3-(1-carboxymethyltetrazol-5-ylthiomethyl)-3-cephem-4-carboxylic acid.

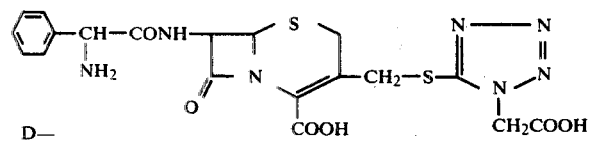

A solution of 0.55 g. (0.0022 mole) of D-(−)-α-tert.-butoxycarboxamidophenylacetic acid and 0.22 g. (0.0022 mole) of triethylamine (TEA) in 17 ml. of tetrahydrofuran (THF) at 0° was stirred vigorously with 0.300 g. (0.0022 mole) of isobutyl chloroformate. The mixture was stirred for 30 min. at 0° and a solution of 0.0022 mole of 7-amino-3-(1-carboxymethyltetrazol-5-ylthiomethyl)-3-cephem-4-carboxylic acid and 0.445 g. (0.0044 mole) of TEA in 6.8 ml. of 50% THF was added. The resulting solution was stirred for 2 hr. at 25° and then the THF evaporated at 40° at 15 mm to an oil. The oil was washed 2×50 ml. of ether, diluted in half with water and acidified to pH 3.0 with dilute hydrochloric acid. The mixture was stirred for 1 hr. in an ice-bath and the product was extracted into 75 ml. of ethyl acetate. The extract was washed with 2×20 ml. of water and 2×50 ml. of saturated sodium chloride solution. The ethyl acetate was evaporated at 35° at 15 mm. to an oil and triturated with Skellysolve B to yield 480 mg. (35.3%) of 7-(D-α-tert.-butoxycarboxamidophenylacetamido)-3-(1-carboxymethyltetrazol-5-ylthiomethyl)-3-cephem-4-carboxylic acid. This sample was added to 1 ml. of trifluoroacetic acid and the solution was stirred for 1 hr. at 0° and then diluted with 50 ml. of ether. The salt was collected, dissolved in 10 ml. of $H_2O$ and adjusted to pH 4.0 with dilute ammonium hydroxide ($NH_4OH$). The product was collected, washed with water and acetone and dried in vacuo over $P_2O_5$ for 18 hr. at 25° to yield 150 mg. (23.96%) of 7-(D-α-aminophenylacetamido)-3-(1-carboxymethyltetrazol-5-ylthiomethyl)-3-cephem-4-carboxylic acid; m.p. >180°, slow decomp. The IR and NMR spectra were consistent for the structure.

Anal Calcd. for $C_{19}H_{19}N_7O_6S_2 \cdot 1\frac{1}{2}H_2O$: C, 42.84; H, 4.16; N, 18.41. Found: C, 43.17; H, 4.12; N, 16.74.

EXAMPLE 4

7-(2-Aminomethyl-1,4-cyclohexadienylacetamido)-3-(1-carboxymethyltetrazol-5-ylthiomethyl)-3-cephem-4-carboxylic acid.

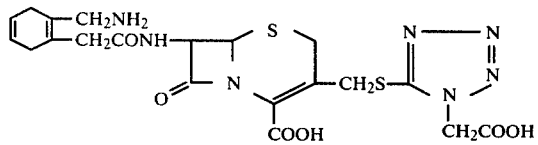

A solution of 0.80 g. (0.003 mole) of 2-t-butoxycarbonylaminomethyl-1,4-cyclohexadienylacetic acid and 0.303 g. (0.003 mole) of triethylamine in 19.2 ml. of THF was stirred at 0° and 0.41 g. (0.003 mole) of isobutyl chloroformate was added. The mixture was stirred for 30 min. at 0° and added to a solution of 0.003 mole of 7-amino-3-(1-carboxymethyltetrazol-5-ylthiomethyl)-3-cephem-4-carboxylic acid and 0.61 g. (0.006 mole) of TEA in 9.2 ml. of 50% THF. The resulting solution was stirred for 1½ hr. at 25°. The tetrahydrofuran was evaporated at 30° at 15 mm and the residue was washed 2×30 with ether and then diluted in half with water. The solution was acidified to pH 3.5 with dilute hydrochloric acid and the product was collected, dried for 18 hr. in vacuo over $P_2O_5$ at 25° to yield 1.55 g. (54.0%) of white powder. A total of 3.4 ml. of trifluoroacetic acid was added to the above 7-(α-(2-t-butoxycarbonylaminomethyl-1,4-cyclohexadienylacetamido)-3-(1-carboxymethyltetrazol-5-ylthiomethyl)-3-cephem-4-carboxylic acid and stirred for 1 hr. at 0°. The solution was diluted with 150 ml. ether and the precipitate was collected by filtration. The trifluoroacetate salt was suspended in 3.4 ml. of water and adjusted to pH 4.5 with dilute ammonium hydroxide. The gummy residue was triturated with water, collected and washed with water and acetone. The product was dried 18 hr. in vacuo over $P_2O_5$ at 25° to yield 53 mg. (15.72%) 7-(2-aminomethyl-1,4-cyclohexadienylacetamido)-3-(1-carboxymethyltetrazol-5-ylthiomethyl)-3-cephem-4-carboxylic acid; m.p. >160°, slow decomp.

Anal. Calcd. for $C_{20}H_{23}N_7O_6S_2 \cdot \frac{1}{2}H_2O$; C, 45.18; H, 4.55; N, 18.44. Found: C, 45.46; H, 4.68; N, 17.09.

The IR and NMR spectra were consistent for the structure.

EXAMPLE 5

7-(α-Amino-4-hydroxyphenylacetamido)-3-(1-carboxymethyltetrazol-5-ylthiomethyl-3-cephem-4-carboxylic acid.

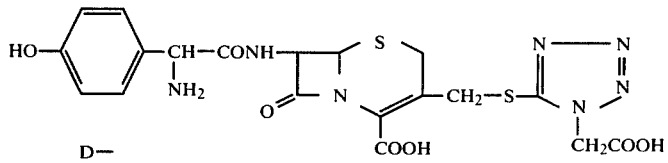

To a solution of 2.7 g. (0.01 mole) of D-(−)-N-tert-butoxycarbonyl-p-hydroxyphenylglycine in 92 ml. of tetrahydrofuran was added 1.1 g. (0.01 mole) of N-methylmorpholine. The solution was cooled to 0° and 1.4 g. (0.01 mole) of isobutylchloroformate was added all at once. The stirring was continued for 10 minutes and the mixed anhydride solution was added to a 0° solution of 3.7 g. (0.01 mole) of 7-amino-3-(1-carboxymethyltetrazol-5-ylthiomethyl)-3-cephem-4-carboxylic acid and 1.1 g. (0.01 mole) of N-methylmorpholine in 50 ml. of water. The solution was stirred for 1 hr. and the tetrahydrofuran was evaporated at 30° (15 mm) to a total volume of 45 ml. The solution was lowered to pH 2 with 1:1 phosphoric acid and extracted with ethyl acetate, washed with water and the solvent was azeotroped to a glassy solid at 30° (15 mm). The residue was triturated with ether to remove any starting acid and collected by filtration. This was hydroscopic and was transferred immediately to 5 ml. of trifluoroacetic acid and stirred for 1 hr. at 27°. The solution was diluted with 25 ml. of ether and the product was collected by filtration and suspended in 5 ml. of water. The mixture was adjusted to pH 3 with conc. ammonium hydroxide and diluted with 10 ml. of isopropanol. The light tan solid was collected by filtration and dried in vacuo over $P_2O_5$ for 24 hr. to yield 300 mg. 7-(α-amino-4-hydroxyphenylacetamido)-3-(1-carboxymethyltetrazol-5-ylthiomethyl-3-cephem-4-carboxylic acid. M.p. 175° slow decomp. Anal. Calcd. for $C_{19}H_{19}N_7O_7S_2 \cdot \frac{3}{4}$ i-$C_3H_7O$: C, 42.78; H, 4.44; N, 17.32. Found: C, 42.86; H, 4.55; N, 15.39. The IR and NMR spectra were consistant for the structure. The NMR spectrum did show the presence of .75 mole isopropyl alcohol in the product.

EXAMPLE 6

7-Phenoxyacetamido-3-(1-carboxymethyltetrazol-5-ylthiomethyl)-3-cephem-4-carboxylic acid by thiolation of 7-phenoxyacetamidocephalosporanic acid Sodium 7-phenoxyacetamidocephalosporanate (0.27 mole) is suspended in 1000 ml. of 0.1 M phosphate buffer pH 6.4 to which is added 0.31 mole disodium 1-carboxymethyl-5-mercaptotetrazole. The solution is heated at 55° C. under a nitrogen atmosphere for 5 hr. After 1 hr. the pH is adjusted to 6.4 by addition of a small amount of 40% $H_3PO_4$. At the end of the 5 hr.

heating period, the solution is cooled to 23° C. and the pH adjusted to 2 by addition of 3 N HCl under a layer of ethyl acetate. The product is extracted into ethyl acetate and stirred for 15 min. at 23° C. with 2 g. of ("Darco KB") decolorizing charcoal. It is then filtered through a pad of diatomaceous earth ("Celite") and the ethyl acetate removed under vacuum to leave an oil which is triturated to a solid with diethyl ether, collected by filtration and dried over $P_2O_5$ under vacuum to yield solid 7-phenoxyacetamido-3-(1-carboxymethyl-tetrazol-5-ylthiomethyl)-3-cephem-4-carboxylic acid.

Samples of the compounds prepared in Examples 1, 2, 3, 4 and 5 after solution in water and dilution with Nutrient Broth were found to exhibit the following Minimum Inhibitory Concentrations (M.I.C.) in mcg./ml. versus the indicated microorganisms as determined by overnight incubation at 37° C. by Tube Dilution.

In Vitro Antibacterial Activity
M.I.C. (μg./ml.)

| Organisms | Ex. 1 (soluble at ≧250 mg/ml as Na+ salt) | Ex. 2 | Ex. 3 | Ex. 4 | Ex. 5 |
|---|---|---|---|---|---|
| Str. pneumoniae* ($10^{-3}$)** | A9585 | 0.13 | 0.6 | 0.6 | 0.06 | 0.25 |
| Str. pyogenes* ($10^{-3}$) | A9604 | 0.13 | 0.6 | 0.6 | 0.13 | 1 |
| S. aureus Smith ($10^{-4}$) | A9537 | 1 | 1.3 | 2.5 | 0.5 | >1 |
| S. aureus-50% serum ($10^{-4}$) | A9537 | 4 | 16 | 32 | >0.5 | 16 |
| S. aureus BX1633 ($10^{-3}$) | A9606 | 1 | 2.5 | >2.5 | 1.3 | 8 |
| S. aureus BX1633 ($10^{-2}$) | A9606 | 2 | 4 | 16 | 2.5 | 8 |
| S. aureus Meth-Res ($10^{-3}$) | A15097 | 4 | 8 | 16 | 4 | 32 |
| Sal. enteritidis ($10^4$) | A9531 | 0.06 | 0.08 | 0.3 | 0.16 | 0.5 |
| E. coli Juhl ($10^{-4}$) | A15119 | 0.5 | 4 | 8 | 1.3 | 8 |
| E. coli ($10^{-4}$) | A9675 | 16 | 32 | 16 | 16 | 32 |
| K. pneumoniae ($10^{-4}$) | A9977 | 0.13 | 1 | 1 | 0.3 | 1 |
| K. pneumoniae ($10^{-4}$) | A15130 | 2 | 32 | 8 | 2 | 8 |
| Pr. mirabilis ($10^{-4}$) | A9900 | 0.13 | 0.5 | 1 | 0.3 | 1 |
| Pr. morganii ($10^{-4}$) | A15153 | 32 | 16 | 32 | 8 | 125 |
| Ps. aeruginosa ($10^{-4}$) | A9843A | >125 | >125 | >125 | >125 | >125 |
| Ser. marcescens ($10^{-4}$) | A20019 | 125 | >125 | >125 | >125 | >125 |
| Ent. cloacae ($10^{-4}$) | A9656 | >125 | >125 | >125 | >125 | >125 |
| Ent. cloacae ($10^{-4}$) | A9657 | 0.25 | 2 | 1 | 0.3 | 2 |
| Ent. cloacae ($10^{-4}$) | A9659 | 32 | >125 | 63 | 32 | 125 |

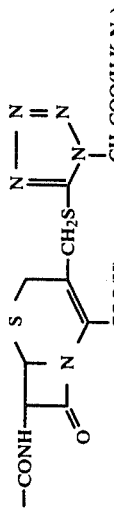

$$R-CONH-\!\!\begin{array}{c}\text{(β-lactam–cephem structure with side chain)}\\ CH_2S-\text{thiadiazole-}N-CH_2COO(H,K,Na)\\ COO(H)(K)(Na)\end{array}$$

R=: (Ex. 1) 2-(aminomethyl)cyclohexyl-CH₂–; (Ex. 2) φ-CH(OH)–; (Ex. 3) φ-CH(NH₂)–; (Ex. 4) 2-(aminomethyl)cyclohexenyl-CH₂–; (Ex. 5) 4-hydroxycyclohexyl-CH(NH₂)–

*45% Antibiotic Assay Broth + 50% Nutrient Broth + 5% serum
**Dilution of overnight broth culture

FORMULATION OF INJECTABLE PRODUCTS

In situ preparation of monosodium salt of 7-(2-aminomethylphenylacetamido)-3-(1-carboxymethyltetrazol-5-ylthiomethyl)-3-cephem-4-carboxylic acid:

(A) 2.5 grams of 7-(2-aminomethylphenylacetamido)-3-(1-carboxymethyltetrazol-5-ylthiomethyl)-3-cephem-4-carboxylic acid (zwitterion) is suspended in 8.5 ml. of water with rapid stirring, sodium citrate or $Na_2HPO_4$ or $Na_3PO_4$ or other suitable "bases" are added until a solution is obtained (the pH should not be over 7.8). The amount of added "base" is noted.

(B) a physical mixture of 2.5 grams of 7-(2-aminomethylphenylacetamido)-3-(1-carboxymethyltetrazol-5-ylthiomethyl)-3-cephem-4-carboxylic acid and the solid "base" in proportions determined in "A" above is made. The later addition of water to obtain various concentrations of 7-(2-aminomethylphenylacetamido)-3-(1-carboxymethyltetrazol-5-ylthiomethyl)-3-cephem-4-carboxylic acid gives a solution of in situ prepared monosodium salt of 7-(2-aminomethylphenylacetamido)-3-(1-carboxymethyltetrazol-5-ylthiomethyl)-3-cephem-4-carboxylic acid.

This procedure may be desirable as trihydrate of monosodium salt of 7-(2-aminomethylphenylacetamido)-3-(1-carboxymethyltetrazol-5-ylthiomethyl)-3-cephem-4-carboxylic acid is not as stable at elevated temperatures as is the free-acid 7-(2-aminomethylphenylacetamido)-3-(1-carboxymethyltetrazol-5-ylthiomethyl)-3-cephem-4-carboxylic acid (zwiterion) monohydrate.

With regard to the stability of 7-(o-aminomethylphenylacetamido)-3-(1-methyl-1,2,3,4-tetrazol-5-ylthiomethyl)-3-cephem-4-carboxylic acid solutions at room temperature and at pH 10.3 (the lowest pH able to dissolve 150 mg./ml.) an almost instantaneous 50% loss of bioactivity is noted. An additional 21% activity is lost in the next 30 minutes.

By contrast, a solution containing 125.0 mg./ml. of the trihydrate of monosodium salt of 7-(2-aminomethylphenylacetamido)-3-(1-carboxymethyltetrazol-5-ylthiomethyl)-3-cephem-4-carboxylic acid at pH 7.0 showed no significant loss at room temperature for at least 24 hours.

The compound entitled 7-(o-aminomethylphenylacetamido)-3-(1-methyl-1,2,3,4-tetrazol-5-ylthiomethyl)-3-cephem-4-carboxylic acid of example 1 and claim 2 of U.S. Pat. No. 3,766,175 is a very potent cephalosporin exhibiting a highly desirable spectrum of activity particularly against certain Gram-negative organisms. Unfortunately, this zwitterion exhibits quite a low solubility in water and particularly in the blood stream which means at about pH 7.2 or thereabouts. To be more specific, attempts to measure this solubility gave results in the range of about 1.0–3.0 mg./ml. in both buffered aqueous media and in dog urine at room temperature. The pH of fresh beagle dog urine is 7.6. This raises a question as to the possible toxic effect in man of the administration of this zwitterion because of the fact that it is assumed that it will precipitate in crystalline form in the kidneys as it is concentrated therein during excretion. This, in man, would be highly undesirable. Conventional attempts to solve this prospective problem by the use of ordinary water soluble forms and derivatives of 7-(o-aminomethylphenylacetamido)-3-(1-methyl-1,2,3,4-tetrazol-5-ylthiomethyl)-3-cephem-4-carboxylic acid have proven unsuccessful because of conversion in the body of the salt or derivative to the zwitterion which then exhibits its natural low solubility in aqueous media and the blood. It was an objective of the present invention to solve this problem without loss of the valuable biological activity of 7-(o-aminomethylphenylacetamido)-3-(1-methyl-1,2,3,4-tetrazol-5-ylthiomethyl)-3-cephem-4-carboxylic acid. After various failures the problem was solved by the provision according to the present invention of 7-(2-aminomethylphenylacetamido)-3-(1-carboxymethyltetrazol-l5-ylthiomethyl)-3-cephem-4-carboxylic acid which has the desired properties. To be more specific a sample of 7-(2-aminomethylphenylacetamido)-3-(1-carboxymethyltetrazol-5-ylthiomethyl)-3-cephem-4-carboxylic acid in pH 7.0 phosphate buffer at 25° C. exhibited a solubility in mg./ml. greater than 15.3 and less than 13.6; in this instance the capacity of the buffer was not sufficient and the pH dropped to 6.48. Thus the 7-(2-aminomethylphenylacetamido)-3-(1-carboxymethyltetrazol-5-ylthiomethyl)-3-cephem-4-carboxylic acid provided by the present invention even in its zwitterionic form is too soluble in the bood stream to crystallize in the kidneys and thereby cause fear of toxic results in at least some patients.

In addition, as set forth above the combination of the lack of aqueous solubility presented a problem which solved by the preparation of the trihydrate of monosodium salt of 7-(2-aminomethylphenylacetamido)-3-(1-carboxymethyltetrazol-5-ylthiomethyl)-3-cephem-4-carboxylic acid of the present invention which exhibits such solubility at pH's suitable for injection in man such as about pH 7 and still exhibits satisfactory solubility in the blood stream and the fluids in the kidney even if converted in the body to the zwitterionic form.

We claim:

1. A compound having the formula

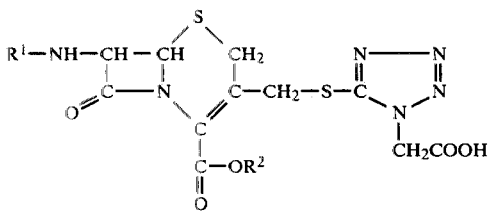

wherein $R^1$ is hydrogen and $R^2$ is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl.

2. The compound of claim 1 wherein $R^2$ is pivaloyloxymethyl.

3. The compound of claim 1 wherein $R^2$ is acetoxymethyl.

4. The compound of claim 1 wherein $R^2$ is methoxymethyl.

5. The compound of claim 1 wherein $R^2$ is acetonyl.

6. The compound of claim 1 wherein $R^2$ is phenacyl.

7. The compound of claim 1 wherein $R^2$ is p-nitrobenzyl.

8. The compound of claim 1 wherein $R^2$ is $\beta,\beta,\beta$-trichloroethyl, 3-phthalidyl or 5-indanyl.

9. A nontoxic pharmaceutically acceptable salt of a compound of claim 1.

10. A compound having the formula

11. A compound of the formula:
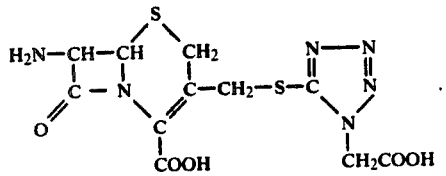
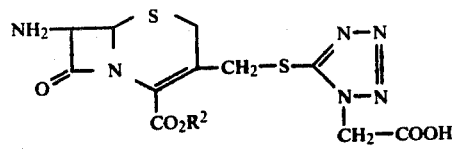
in which R² is hydrogen or pivaloyloxymethyl, acetoxymethyl, methoxymethyl, acetonyl, phenacyl, p-nitrobenzyl, β,β,β-trichloroethyl, 3-phthalidyl or 5-indanyl, or a non-toxic pharmaceutically acceptable salt thereof.